(12) United States Patent
Dieterle et al.

(10) Patent No.: US 7,807,853 B2
(45) Date of Patent: Oct. 5, 2010

(54) PROCESS FOR HETEROGENEOUSLY CATALYZED PARTIAL GAS PHASE OXIDATION OF PROPYLENE TO ACRYLIC ACID

(75) Inventors: Martin Dieterle, Mannheim (DE); Armin Diefenbacher, Germersheim (DE); Klaus Joachim Mueller-Engel, Stutensee (DE); Jochen Petzoldt, Weisenheim am Berg (DE)

(73) Assignee: BASF Aktiengesellschaft, Ludwigshafen (DE)

(*) Notice: Subject to any disclaimer, the term of this patent is extended or adjusted under 35 U.S.C. 154(b) by 830 days.

(21) Appl. No.: 11/566,284

(22) Filed: Dec. 4, 2006

(65) Prior Publication Data

US 2007/0149808 A1 Jun. 28, 2007

Related U.S. Application Data

(60) Provisional application No. 60/752,369, filed on Dec. 22, 2005.

(30) Foreign Application Priority Data

Dec. 22, 2005 (DE) .................. 10 2005 062 026

(51) Int. Cl.
- *C07C 51/16* (2006.01)
- *C07C 69/52* (2006.01)
- *C08F 120/18* (2006.01)

(52) U.S. Cl. ............... 562/545; 562/546; 562/547; 560/225; 526/329.7

(58) Field of Classification Search .............. 562/532, 562/545, 546, 547; 526/187, 329.7; 560/225
See application file for complete search history.

(56) References Cited

U.S. PATENT DOCUMENTS

| | | | |
|---|---|---|---|
| 4,413,147 A | 11/1983 | Khoobiar | |
| 4,532,365 A | 7/1985 | Khoobiar | |
| 4,535,188 A | 8/1985 | Khoobiar | |
| RE32,082 E | 2/1986 | Khoobiar | |
| 6,767,976 B2 * | 7/2004 | Hamada et al. | ............. 526/187 |
| 6,781,017 B2 | 8/2004 | Machhammer et al. | |
| 7,019,168 B2 | 3/2006 | Dieterle et al. | |
| 7,238,827 B2 | 7/2007 | Hechler et al. | |
| 2004/0063988 A1 | 4/2004 | Hechler et al. | |
| 2004/0116741 A1 | 6/2004 | Nordhoff et al. | |
| 2004/0181083 A1 | 9/2004 | Proll et al. | |
| 2004/0199001 A1 | 10/2004 | Schindler et al. | |
| 2005/0222459 A1 | 10/2005 | Nordhoff et al. | |
| 2006/0004227 A1 | 1/2006 | Dieterle et al. | |
| 2006/0004229 A1 | 1/2006 | Dieterle et al. | |
| 2006/0258529 A1 | 11/2006 | Diefenbacher et al. | |

FOREIGN PATENT DOCUMENTS

| | | |
|---|---|---|
| DE | 3313573 A1 | 10/1983 |
| DE | 3521458 A1 | 12/1985 |
| DE | 10131297 A1 | 1/2003 |
| DE | 10245585 A1 | 4/2004 |
| DE | 10 2005 010 111 A1 | 9/2006 |
| DE | 102005 013039 A1 | 9/2006 |
| DE | 102005009885 A1 | 9/2006 |
| DE | 102005022798 A1 | 11/2006 |
| GB | 2160543 A | 12/1985 |
| WO | WO 01/96270 A2 | 12/2001 |
| WO | WO 02/055469 A1 | 7/2002 |
| WO | WO 03/011804 A2 | 2/2003 |
| WO | WO 03/078378 A1 | 9/2003 |
| WO | WO 2004/031106 A1 | 4/2004 |
| WO | WO 2004/085368 A2 | 10/2004 |

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

A process for heterogeneously catalyzed partial gas phase oxidation of propylene to acrylic acid in the absence of propane as an inert diluent gas, in which, in the starting reaction gas mixture, cyclopropane is substantially avoided as an impurity and crude propylene is used additionally as a propylene source.

38 Claims, No Drawings

PROCESS FOR HETEROGENEOUSLY CATALYZED PARTIAL GAS PHASE OXIDATION OF PROPYLENE TO ACRYLIC ACID

CROSS-REFERENCE TO RELATED APPLICATIONS

The present application claims priority to U.S. provisional patent application 60/752,369, filed on Dec. 22, 2005, and German patent application DE 102005062026.4, filed on Dec. 22, 2005, which are incorporated herein by reference in their entireties.

The present invention relates to a process for heterogeneously catalyzed partial gas phase oxidation of propylene to acrylic acid, in which, in a first reaction zone, a starting reaction gas mixture 1 which comprises propylene and molecular oxygen as reactants and at least propane as an inert diluent gas and comprises the molecular oxygen and the propylene in a molar $O_2:C_3H_6$ ratio of $\geq 1$ is first, in a first reaction stage at elevated temperature, conducted through at least one first catalyst bed whose catalysts have at least one multimetal oxide comprising Mo, Fe and Bi as the active composition in such a way that the propylene conversion in single pass through the catalyst bed is $\geq 90$ mol % and the accompanying selectivity $S^{AC}$ of acrolein formation and of acrylic acid by-product formation together is $\geq 80$ mol %, the temperature of the product gas mixture 1 leaving the first reaction stage is reduced if appropriate by direct cooling or by indirect cooling or by direct and indirect cooling, and, if appropriate, secondary gas in the form of molecular oxygen or inert gas or molecular oxygen and inert gas is added to product gas mixture 1, and then product gas mixture 1, as a starting reaction gas mixture 2 which comprises acrolein and molecular oxygen as reactants and at least propane as an inert diluent gas and comprises the molecular oxygen and the acrolein in a molar $O_2:C_3H_4O$ ratio of $\geq 0.5$, in a second reaction stage at elevated temperature and with formation of a product gas mixture 2, is conducted through at least one second catalyst bed whose catalysts have at least one multimetal oxide comprising Mo and V as the active composition in such a way that the acrolein conversion in single pass through the catalyst bed is $\geq 95$ mol % and the selectivity $S^{AA}$ of acrylic acid formation assessed over both reaction stages, based on propylene converted, is $\geq 70$ mol %.

As a partial oxidation product of propylene, acrylic acid is a significant monomer which finds use as such or in the form of its alkyl esters for obtaining polymers suitable, for example, as adhesives, or water-superabsorbing polymers (cf., for example, WO 03/011804, DE-A 102 45 585, EP-A 1 611 078, DE-A 10 2005 013 039, DE-A 10 2005 010 111, WO 02/055469 and WO 03/078378).

The preparation of acrylic acid by heterogeneously catalyzed two-stage partial oxidation of propylene is known (cf., for example, DE-A 102 45 585, WO 03/011804, DE-A 101 31 297, WO 01/96270).

The propylene required as a starting substance for this procedure is typically added as a constituent of crude propylene. In contrast to chemically pure propylene, crude propylene should be understood in this document to mean propylene which, in addition to propylene, also comprises at least two (or at least three, or at least four) further constituents (impurities) other than propane and cyclopropane (and preferably also other than water and molecular oxygen). Useful such impurities, depending on the preparation route of the crude propylene, are, for example (cf., for example, DE-A 101 31 297): ethane, methane, $C_4$ hydrocarbons, acetylene, ethylene, water, $O_2$, compounds comprising sulfur, compounds comprising chlorine, $CO_2$, CO, propadiene, propyne, $C_{\geq 5}$ hydrocarbons, compounds comprising carbonyl groups, and so forth. For example, crude propylene may also be the product gas mixture of a heterogeneously catalyzed partial propane dehydrogenation (cf., for example, DE-A 102 45 582 and DE-A 10 2005 022 798). In particular, crude propane in this document should additionally be such that propylene present therein, to an extent of at least 90 mol %, has not yet passed through a heterogeneously catalyzed partial oxidation to acrylic acid. Preferably in accordance with the invention, crude propylene, in addition to the above, should not stem from a heterogeneously catalyzed partial dehydrogenation of propane (or not be recyclable to such a partial dehydrogenation). Most preferably in accordance with the invention, crude propylene, in addition to the above, should stem neither from a heterogeneously catalyzed dehydrogenation of propane nor from a heterogeneously catalyzed partial oxydehydrogenation of propane (or not be recyclable to such partial dehydrogenations). Advantageously in accordance with the invention, crude propylene comprises propylene to an extent of at least 90% by weight (or to an extent of at least 90% by volume). More preferably, the aforementioned propylene contents of crude propylene are, advantageously in accordance with the invention, at least 92% by weight (or at least 92% by volume), or at least 94% by weight (or at least 94% by volume), or at least 95% by weight (or at least one 95% by volume), or at least 96% by weight (or at least 96% by volume), advantageously at least 97% by weight (or at least 97% by volume), preferably $\geq 98\%$ by weight (or $\geq 98\%$ by volume) and more preferably $\geq 99$ (or $\geq 99.5$) % by weight (or $\geq 99$ (or $\geq 99.5$) % by volume).

It is also advantageous for the process according to the invention when the crude propylene to be used consists of propylene to an extent of $\geq 90\%$ by weight and of propane and propylene to an extent of $\geq 97\%$ by weight (or to an extent of $\geq 98\%$ by weight, preferably to an extent of $\geq 99\%$ by weight).

It is also favorable for the process according to the invention when the crude propylene to be used consists of propylene to an extent of $\geq 94\%$ by weight and of propane and propylene to an extent of $\geq 97\%$ by weight (or to an extent of $\geq 98\%$ by weight, preferably to an extent of $\geq 99\%$ by weight).

It is also particularly favorable for the process according to the invention when the crude propylene to be used consists of propylene to an extent of $\geq 96\%$ by weight (better to an extent of $\geq 97\%$ by weight) and of propane and propylene to an extent of $\geq 98\%$ by weight (or to an extent of $\geq 99\%$ by weight).

It is very particularly favorable for the process according to the invention when the crude propylene to be used consists of propylene to an extent of $\geq 99.6\%$ by weight and of propane and propylene to an extent of $\geq 99.7\%$ by weight.

It is possible in principle to remove all impurities present in crude propylene from propylene present therein (cf., for example, DE-A 35 21 458 and DE-A 102 45 585). However, this is not necessary when the impurities behave inertly in the heterogeneously catalyzed partial oxidation of propylene to acrylic acid. When the latter property exists, the impurities simply act as inert diluent gases in the starting reaction gas mixture during the heterogeneously catalyzed partial oxidation of propylene to acrylic acid (cf. WO 01/96270 and DE-A 33 13 573).

In this document, this refers quite generally to those gases which, in the course of the partial oxidation, each alone, remain chemically unchanged to an extent of at least 95 mol %, preferably to an extent of at least 97 mol % and most preferably to an extent of 99 mol % or more.

In a removal of acrylic acid from the product gas mixture of the partial oxidation (this is typically effected by converting the acrylic acid from the product gas mixture into the condensed phase), these inert gases typically remain as residual gas in the gas phase and can thus be removed from the acrylic acid target product after the partial oxidation in a comparatively simpler manner than would be the case in a removal of the propylene prior to the partial oxidation. The aforementioned applies correspondingly to impurities present in other inert diluent gases if these inert diluent gases are added to the starting reaction gas mixture for the partial oxidation as such crude inert diluent gases.

The technical literature has hitherto regarded the propanes to be such inert gases in relation to the partial oxidation of propylene to acrylic acid. The considerations in this regard even go to the extent of replacing propylene as the raw material for preparing acrylic acid with propane as such a raw material. In this case, propane is dehydrogenated partially to propylene in a first step and the propylene formed in the first step is subsequently partially oxidized to acrylic acid under heterogeneous catalysis in the presence of the unconverted propane. Normally, propane in such a resulting starting reaction gas mixture even forms the main constituent. Recycling of the residual gas which comprises unconverted propane and remains in the condensation of the target product out of the product gas mixture into the dehydrogenation and/or partial oxidation allows the propane in this way finally to be converted fully to acrylic acid (cf., for example DE-A 102 45 585, DE-A 10 2005 009 885, DE-A 10 2005 010 111). Although a vanishing amount of the propane (of the order of magnitude of 0.01% by weight based on its use amount) can be converted to propionic acid (which is an undesired companion to acrylic acid merely owing to its unpleasant odor even in the smallest amounts and also owing to its inability to polymerize in a free-radical manner), such low by-product formation can be counteracted, for example, by diluting starting reaction gas mixture 1 additionally with an inert diluent gas other than propane (for example $N_2$, $H_2O$, $CO_2$, noble gas, mixtures of these gases, etc.) (cf., for example, WO 01/96270).

However, the above considerations are no longer valid when the crude gas impurity does not behave inertly in a heterogeneously catalyzed partial oxidation of propylene to acrylic acid, but rather is converted to a by-product of acrylic acid formation in significant amounts. This is attributable to the fact that the by-product formed normally cannot be discharged as a target product impurity with the target product. Instead, even minor target product impurities in many cases have a troublesome effect with a view to the desired target product use (for example, in the case of use of the acrylic acid for preparing polyacrylic acids and/or their partly and/or fully neutralized alkali metal salts which are used predominantly as water-superabsorbing materials in the hygiene sector; or in the case of use of the acrylic acid for preparing its alkyl esters and the use of the latter for preparing polymers suitable as adhesives) and then have to be removed from the target product (or the condensed phase comprising it) in a comparatively costly and inconvenient manner by means of thermal separation processes (or vice versa). In such cases, attempts will then appropriately be made, for example, to remove the appropriate propylene impurity prior to the partial oxidation. This is true in particular when the crude gas impurity is converted to a by-product which is comparatively similar to acrylic acid in the course of the heterogeneously catalyzed partial oxidation to acrylic acid.

In many cases, a parallel procedure is also employed for reasons of economic viability. In other words, a portion of the crude gas impurity is removed prior to the use of crude gas for the partial oxidation, and the remaining portion is removed from the target product as a by-product formed after the partial oxidation has been carried out (or vice versa). When the remaining portion is small enough, the by-product formed therefrom can, if appropriate, also be discharged with the target product. Possible removal processes are in particular thermal separation processes.

Thermal separation processes are understood to mean those processes in which at least two substance phases different from one another (for example liquid/liquid; gaseous/liquid; solid/liquid; gaseous/solid, etc.) are generated and contacted with one another. Owing to the inequilibrium existing between the phases, heat and mass transfer which ultimately causes the desired separation (removal) takes place between them. The term thermal separation processes reflects that it requires either the withdrawal or the supply of heat to obtain the formation of the substance phases and/or that the withdrawal or the supply of thermal energy promotes or maintains the mass transfer.

Thermal separation processes are therefore, for example, distillations, rectifications, crystallations, extractions, azeotropic distillations, azeotropic rectifications, stripping, desorption, etc. (cf. also WO 04/063138). Among these, crystallizative thermal separation processes are considered to be particularly capital-intensive.

It has now been found in the course of in-house studies that, surprisingly, cyclopropane, a common companion of propylene in crude propylene and of propane in crude propane, in contrast to n-propane (without further addition, propane in this document always means n-propane) is not an inert gas in a heterogeneously catalyzed partial oxidation of propylene to acrylic acid as described at the outset. In the course of heating to from 100 to 200° C. in the presence of catalysts (e.g. Pt), cyclopropane is isomerized to propylene (for example Lehrbuch der Organischen Chemie [Textbook of organic chemistry], Beyer•Walter, Hirzel Verlag Stuttgart, page 390, 1991). In the course of an heterogeneously catalyzed partial oxidation of propylene to acrylic acid as described at the outset, however, it behaves quite differently to propylene and does not react virtually exclusively to give acrylic acid like the latter, but rather, in an entirely unexpected manner and to a high and surprisingly considerable extent, to give propionic acid.

However, this is particularly difficult to remove from acrylic acid in thermal separation processes (at 1 bar, b.p. of acrylic acid: 141° C., of propionic acid: 141.35° C.). Only by crystallization are appropriate depletion coefficients achievable. It was therefore an object of the present invention to work advantageously with the above-described surprising chance finding in the context of a preparation of, for example, acrylic acid very low in propionic acid via the route of a two-stage heterogeneously catalyzed partial oxidation of propylene to acrylic acid. This is also against the background that the aforementioned isomerization to propylene is a simple means of removing the cyclopropane in crude gases prior to their use for the partial oxidation. In principle, cyclopropane can also be removed by rectification from propylene or propane, given that the relevant boiling points are sufficiently different from one another at standard pressure (propylene b.p.=−47° C.; propane b.p.=−44.5° C. and cyclopropane b.p.=−32.8° C.). The aforementioned objective and its solution is of particular interest in particular when at least a portion of the residual gas which remains in the removal of acrylic acid from the product gas mixture of the partial oxidation and would comprise incompletely converted cyclopropane in the partial oxidation is recycled at least partly as cycle gas into the partial oxidation as a constituent of the corresponding starting reaction gas mixture, given that such a cycle gas method in continuous operation would be accompanied by accumulation of the cyclopropane in the starting reaction gas mixture.

As a solution to the object of the invention, a process has been found for heterogeneously catalyzed partial gas phase oxidation of propylene to acrylic acid, in which, in a first reaction zone, a starting reaction gas mixture 1 which comprises propylene and molecular oxygen as reactants and at least propane as an inert diluent gas and comprises the molecular oxygen and the propylene in a molar $O_2:C_3H_6$ ratio of $\geqq 1$ is, in a first reaction stage at elevated temperature, conducted through at least one first catalyst bed whose catalysts have at least one multimetal oxide comprising Mo, Fe and Bi as the active composition in such a way that the propylene conversion $C^P$ in single pass through the catalyst bed is $\geqq 90$ mol % and the accompanying selectivity $S^{AC}$ of acrolein formation and of acrylic acid by-product formation together is $\geqq 80$ (preferably $\geqq 85$, or $\geqq 90$) mol %, the temperature of the product gas mixture 1 leaving the first reaction stage is reduced if appropriate by direct cooling or by indirect cooling or by direct and indirect cooling, and, if appropriate, secondary gas in the form of molecular oxygen or inert gas or molecular oxygen and inert gas is added to product gas mixture 1, and then product gas mixture 1, as a starting reaction gas mixture 2 which comprises acrolein and molecular oxygen as reactants and at least propane as an inert diluent gas and comprises the molecular oxygen and the acrolein in a molar $O_2:C_3H_4O$ ratio of $\geqq 0.5$, in a second reaction stage at elevated temperature and with formation of a product gas mixture 2, is conducted through at least one second catalyst bed whose catalysts have at least one multimetal oxide comprising Mo and V as the active composition in such a way that the acrolein conversion $C^A$ in single pass through the catalyst bed is $\geqq 95$ mol % and the selectivity $S^{AA}$ of acrylic acid formation assessed over both reaction stages, based on propylene converted, is $\geqq 70$ (preferably $\geqq 75$ or $\geqq 80$) mol %, wherein starting reaction gas mixture 1, based on the molar amount of propane present therein, comprises $\leqq 3$ mol % of cyclopropane and has been obtained with additional use of crude propylene.

The process according to the invention is of significance especially when it is operated such that $C^A$ is $\geqq 96$ mol %, or $\geqq 97$ mol %, or $\geqq 98$ mol %, or $\geqq 98.5$ mol %, or $\geqq 99$ mol %, or $\geqq 99.5$ mol %, or $\geqq 99.8$ mol % or more. The aforementioned is especially true when the first reaction stage is simultaneously operated such that $C^P$ is $\geqq 91$ mol %, or $\geqq 92$ mol %, or $\geqq 93$ mol %, or $\geqq 94$ mol %, or $\geqq 95$ mol %, or $\geqq 96$ mol %, or $\geqq 97$ mol %, or $\geqq 98$ mol %, or $\geqq 99$ mol %. This is caused by the aforementioned conversions (they always relate to single pass of the reaction gas mixture through the catalyst bed) with the same catalyst system normally being achieved when the reaction temperature in the particular reaction stage is selected at an elevated level. However, elevated temperatures are especially also beneficial for the conversion of cyclopropane to propionic acid.

The process according to the invention develops its advantageousness especially when the content in starting reaction gas mixture 1 of cyclopropane, based on propane present therein, is $\leqq 2.5$ mol %, better $\leqq 2$ mol %, preferably $\leqq 1.5$ mol %, better $\leqq 1$ mol %, more preferably $\leqq 0.75$ mol %, better $\leqq 0.5$ mol %, even better $\leqq 0.25$ or $\leqq 0.2$ mol %, more advantageously $\leqq 0.17$, or $\leqq 0.15$, or $\leqq 0.1$ mol %. At best, the content in starting reaction gas mixture 1 of cyclopropane is vanishing. However, for reasons of convenience, it will frequently be such that it is, based on propane present in the starting reaction gas mixture, $\geqq 10$ molppb, or $\geqq 50$ molppb, or $\geqq 100$ molppb, or $\geqq 1$ molppm, or $\geqq 10$ molppm.

Processes according to the invention are thus also those in which the cyclopropane content of starting reaction gas mixture 1, based on propane present therein, is from 10 molppm to 8000 molppm, or from 10 molppm to 5000 molppm, or from 100 molppm to 3000 molppm, or from 200 molppm to 2500 molppm, or from 300 molppm to 2000 molppm, or from 400 molppm, or 500 molppm to 1500 molppm, or from 750 molppm to 1250 molppm.

Otherwise, the process according to the invention may be carried out like the processes known per se for two-stage heterogeneously catalyzed partial gas phase oxidation of propylene to acrylic acid (cf., for example, WO 01/36364).

For example, the catalyst beds may be fixed beds or fluidized beds. Preference is given in accordance with the invention to the use of fixed catalyst beds in both reaction stages.

In this document, the loading of the (fixed) catalyst bed with starting reaction gas mixture is understood to mean the amount of starting reaction gas mixture in standard liters (=l (STP); the volume in liters that the appropriate amount of starting reaction gas mixture would take up under standard conditions (i.e. at 25° C. and 1 bar)) which is conducted through one liter of (fixed) catalyst bed per hour. However, the loading of the (fixed) catalyst bed may also be based only on a component of the starting reaction gas mixture. In that case, it is the amount of this component in standard liters which is conducted as a constituent of a appropriate starting reaction gas mixture through one liter of the (fixed) catalyst bed per hour.

Specifically, the realization of the two-stage heterogeneously catalyzed partial oxidation of propylene to acrylic acid to be carried out in accordance with the invention using an inventive starting reaction gas mixture 1 may for example be carried out as described in the documents EP-A 700 714 (first reaction stage; as described there, but also in corresponding countercurrent mode of salt bath and starting reaction gas mixture over the tube bundle reactor), EP-A 700 893 (second reaction stage; as described there, but also in corresponding countercurrent mode), WO 04/085369 (especially this document is considered to be an integral part of this document) (as a two-stage process), WO 04/05363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (two-stage), WO 04/085368 (as a two-stage process), DE-A 10 2004 021 764 (two-stage), WO 04/085362 (first reaction stage), WO 04/085370 (second reaction stage), WO 04/085365 (second reaction stage), WO 04/085367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage is an inventive starting reaction gas mixture 1. Regarding the remaining parameters, the procedure is as in the working examples of the documents mentioned (especially regarding the fixed catalyst beds and reactant loading on the fixed catalyst beds). When there is supply of molecular secondary oxygen between the two reaction stages in the process according to the invention, this is effected preferably in accordance with the invention in the form of air. However, it can also be effected in the form of pure molecular oxygen or else in the form of another mixture of molecular oxygen and of inert gas.

Advantageously in accordance with the invention, secondary oxygen is supplied in such an amount that product gas mixture 2 still comprises unconverted molecular oxygen. However, the amount of molecular oxygen required for the overall process may also already be added to starting reaction gas mixture 1. In general, the molar ratio of molecular oxygen present in starting reaction gas mixture 1 to propylene present in this mixture is $\geq 1$ and $\leq 3$.

Multimetal oxide catalysts which comprise the elements required in accordance with the invention and are suitable for the particular reaction stage of the two reaction stages have been described many times before and are well known to those skilled in the art. For example, EP-A 253 409 refers on page 5 to corresponding U.S. patents. Suitable catalysts for the particular oxidation stage (reaction stage) are also disclosed by DE-A 44 31 957, DE-A 10 2004 025 445 and DE-A 44 31 949. This is especially true of those of the general formula I in the two aforementioned prior art documents. Catalysts usable for the particular oxidation stage (reaction stage) are also disclosed by the documents DE-A 103 25 488, DE-A 103 25 487, DE-A 103 53 954, DE-A 103 44 149, DE-A 103 51 269, DE-A 103 50 812, DE-A 103 50 822.

Possible multimetal oxide active compositions comprising Mo, Bi and Fe for the process according to the invention in the first reaction stage are also the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168, and also the multimetal oxide active compositions specified in EP-A 700 714.

Also suitable for the first reaction stage of the process according to the invention are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This applies in particular to the exemplary embodiments in these documents, and among these particular preference is given to those of EP-A 15565, EP-A 575897, DE-A 197 46 210 and DE-A 198 55 913. Particular emphasis is given in this context to a catalyst according to Example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x$. 10 $SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to Example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of those multimetal oxide active compositions which comprise Mo, Fe and Bi in whose presence the cyclopropane in the first reaction stage is particularly amenable to the undesired side reaction and in the case of whose use the inventive procedure is therefore particularly relevant can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

The aforementioned is true in particular when they are obtained in a manner known per se (see, for example, DE-A 40 23 239) and used in accordance with the invention, for example, shaped in substance to give spheres, rings or cylinders, or else used in the form of coated catalysts, i.e. preshaped inert support bodies coated with the active composition. It will be appreciated that the statement also applies when they are used in powder form as catalysts for the first reaction stage (for example in fluidized bed reactors).

In principle, active compositions of the general formula IV can generally be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and, if appropriate, compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the first reaction stage of the process according to the invention either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A hollow cylinder geometry particularly relevant in accordance with the invention is 5 mm×3 mm×2 mm (external diameter×length×internal diameter), especially in the case of unsupported catalysts.

The pulverulent active composition relevant in accordance with the invention, or its pulverulent precursor composition which is yet to be calcined and/or partially calcined, may of course also be shaped by applying to preshaped inert catalyst supports. The coating of the support bodies to produce the coated catalysts is generally performed in a suitable rotatable vessel, as disclosed, for example, by DE-A 29 09 671, EP-A 293 859 or EP-A 714 700. To coat the support bodies, the powder composition to be applied is appropriately moistened and dried again after application, for example by means of hot air. The coating thickness of the powder composition applied to the support body is frequently selected within the range from 10 to 1000 μm, preferably within the range from 50 to 500 μm and more preferably within the range from 150 to 250 μm.

Useful support materials are the customary porous or non-porous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. It is relevant in accordance with the invention to use substantially nonporous, surface-roughened spherical supports made of steatite whose diameter is from 1 to 10 mm or to 8 mm, preferably from 4 to 5 mm. However, it is also relevant in accordance with the invention to use cylinders whose length is from 2 to 10 mm and whose external diameter is from 4 to 10 mm as support bodies. In the case of rings as support bodies, the wall thickness is also typically from 1 to 4 mm. Annular support bodies to be used in accordance with the invention have a length of from 2 to 6 mm, an external diameter of from 4 to 8 mm and a wall thickness of from 1 to 2 mm. Also relevant in accordance with the invention are rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions relevant in accordance with the invention for the step from propylene to acrolein are also compositions of the general formula V $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \qquad (V)$$

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$a'$=from 0.01 to 8,
$b'$=from 0.1 to 30,
$c'$=from 0 to 4,
$d'$=from 0 to 20,
$e'$=from >0 to 20,
$f'$=from 0 to 6,
$g'$=from 0 to 15,
$h'$=from 8 to 16,
$x'$, $y'$=numbers which are determined by the valency and frequency of the elements in V other than oxygen and
$p$, $q$=numbers whose p/q ratio is from 0.1 to 10, comprising three-dimensional regions of the chemical composition $Y^1_{a'}Y^2_{b'}O_{x'}$ which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions V in accordance with the invention are those in which $Y^1$ is only bismuth.

Among these, preference is given in turn to those of the general formula VI $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \qquad (VI)$$

in which the variables are each defined as follows:

$Z^2$=molybdenum, or tungsten, or molybdenum and tungsten, $Z^3$=nickel and/or cobalt, $Z^4$=thallium, an alkali metal and/or an alkaline earth metal, $Z^5$=phosphorus, arsenic, boron, antimony, tin, cerium and/or lead, $Z^6$=silicon, aluminum, titanium and/or zirconium, $Z^7$=copper, silver and/or gold, $a''$=from 0.1 to 1, $b''$=from 0.2 to 2, $c''$=from 3 to 10, d"=from 0.02 to 2, e"=from 0.01 to 5, preferably from 0.1 to 3, f"=from 0 to 5, g"=from 0 to 10, h"=from 0 to 1, x", y"=numbers which are determined by the valency and frequency of the elements in VI other than oxygen, p", q"=numbers whose p"/q" ratio is from 0.1 to 5, preferably from 0.5 to 2, and very particular preference is given to those compositions VI in which $Z^2_{b''}=(\text{tungsten})_{b''}$ and $Z^2_{12}=(\text{molybdenum})_{12}$.

It is also significant in accordance with the invention when at least 25 mol % (preferably at least 50 mol % and more preferably at least 100 mol %) of the total proportion of $[Y^1_a Y^2_b O_x]_p ([Bi_{a''} Z^2_{b''} O_{x''}]_{p''})$ of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_a Y^2_b O_{x'} [Bi_{a''} Z^2_{b''} O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the second step (the second reaction stage), the heterogeneously catalyzed gas phase partial oxidation of acrolein to acrylic acid, useful active compositions for the catalysts required are, in accordance with the invention, in principle all multimetal oxide compositions comprising Mo and V, for example those of DE-A 100 46 928 and of DE-A 198 15 281.

A multitude thereof which are particularly relevant in accordance with the invention for the undesired reaction of cyclopropane can be encompassed by the general formula VII

  (VII)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are particularly relevant in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly relevant in accordance with the invention are those of the general formula VIII

  (VIII)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are relevant in accordance with the invention are obtainable in a manner known per se, for example disclosed in DE-A 43 35 973 or in EP-A 714 700.

Generally, multimetal oxide active compositions relevant in accordance with the invention for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the inventive acrolein oxidation either in powder form (for example in fluidized bed reactors) or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of relevant unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is, in a manner relevant in accordance with the invention, frequently selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. It is suitable to use substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or of 5.1 mm. However, it is also suitable to use cylinders whose length is from 2 to 10 mm and whose external diameter is from 4 to 10 mm as support bodies. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Also relevant are in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Multimetal oxide active compositions relevant for the inventive "acrolein→acrylic acid" step are also compositions of the general formula IX $$[D]_p[E]_q \tag{IX}$$

in which the variables are each defined as follows:

$D = Mo_{12}V_{a''}Z^1_{b''}Z^2_{c''}Z^3_{d''}Z^4_{e''}Z^5_{f''}Z^6_{g''}O_{x'''}$,
$E = Z^7_{12}CU_{h''}H_{i''}O_{y''}$,
$Z^1$ = W, Nb, Ta, Cr and/or Ce,
$Z^2$ = Cu, Ni, Co, Fe, Mn and/or Zn,
$Z^3$ = Sb and/or Bi,
$Z^4$ = Li, Na, K, Rb, Cs and/or H,
$Z^5$ = Mg, Ca, Sr and/or Ba,
$Z^6$ = Si, Al, Ti and/or Zr,
$Z^7$ = Mo, W, V, Nb and/or Ta, preferably Mo and/or W,
a″ = from 1 to 8,
b″ = from 0.2 to 5,
c″ = from 0 to 23,
d″ = from 0 to 50,
e″ = from 0 to 2,
f″ = from 0 to 5,
g″ = from 0 to 50,
h″ = from 4 to 30,
i″ = from 0 to 20 and
x″, y″ = numbers which are determined by the valency and frequency of the elements in IX other than oxygen and
p, q = numbers other than zero whose p/q ratio is from 160:1 to 1:1, and which are obtainable by separately preforming a multimetal oxide composition E $$Z^7_{12}Cu_{h''}H_{i''}O_{y''} \tag{E}$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_{a''}Z^1_{b''}Z^2_{c''}Z^3_{d''}Z^4_{e''}Z^5_{f''}Z^6_{g''} \tag{D}$$

(starting composition 2) in the desired p:q ratio, drying the aqueous mixture which may result, and calcining the resulting dry precursor composition before or after drying at temperatures of from 250 to 600° C. to give the desired catalyst geometry.

Particularly relevant multimetal oxide compositions IX are those in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are particularly relevant in accordance with the invention for the "acrolein→acrylic acid" step are also those of DE-A 198 15 281, especially having multimetal oxide active compositions of the general formula I of this document.

With relevance in accordance with the invention, unsupported catalyst rings are used for the step from propylene to acrolein and coated catalyst rings for the step from acrolein to acrylic acid.

According to the invention, the reaction temperature in the first reaction stage is appropriately from 270 to 450° C. or from 280 to 420° C., preferably from 300 to 380° C. According to the invention, the reaction temperature in the second reaction stage is appropriately from 200 to 370 or to 320° C., preferably from 220 to 300° C.

The process according to the invention is also of particular relevance when the active compositions for the catalysts of the first reaction stage comprise those whose specific surface area is from 0.1 to 120 m$^2$/g, or from 0.2 to 50 m$^2$/g, or from 1 to 20 m$^2$/g, or from 2 to 10 m$^2$/g.

The process according to the invention is also of particular relevance when the active compositions for the catalysts of the first reaction stage comprise those whose numerically most frequent pore diameter is from 0.1 to 1 µm.

It is also of particular relevance when the aforementioned numerically most frequent pore diameters and one of the aforementioned specific surface areas are present in combination in the active compositions for the catalysts of the first reaction stage.

Moreover, the process according to the invention is of particularly significance when the proportion of different pore diameters in the total pore volume in the active compositions for the catalysts of the first reaction stage has the following distribution:

Pores having diameters in the range from <0.03 µm: $\geq 0$ and $\leq 5\%$ by volume. Pores having diameters in the range from $\geq 0.003$ µm to $\leq 0.1$ µm: $\geq 3$ and $\leq 20\%$ by volume.

Pores having diameters in the range from >0.1 to <1 µm: $\geq 75$ and $\leq 95\%$ by volume and Pores having diameters in the range from $\geq 1$ to $\leq 10$ µm: $\geq 0$ and $\leq 5\%$ by volume.

The total pore volume for first-stage catalyst active compositions relevant in accordance with the invention is typically from 0.1 to 1.00 ml/g, usually from 0.10 to 0.80 ml/g, or from 0.20 to 0.40 ml/g.

Furthermore, the process according to the invention is of particular relevance when the active compositions for the catalysts of the second reaction stage comprise those whose specific surface area is from 0.1 to 150 m$^2$/g, or from 0.2 to 50 m$^2$/g, or from 1 to 20 m$^2$/g, or from 2 to 10 m$^2$/g. In addition, the process according to the invention is of particular relevance when the active compositions for the catalysts of the second reaction stage comprise those whose numerically most frequent pore diameter is from 0.1 to 1 µm.

It is also of particular relevance when the aforementioned numerically most frequent pore diameters and one of the aforementioned specific surface areas are present in combination in the active compositions for the catalysts of the second reaction stage.

The total pore volume for second-stage catalysts relevant in accordance with the invention is typically from 0.10 to 0.90 ml/g, or from 0.20 to 0.80 ml/g, or from 0.30 to 0.70 ml/g.

Moreover, the process according to the invention is of particular significance when the pore distribution in the active compositions for the catalysts of the second reaction stage is such that in each case at least 5% by volume, preferably at least 10% by volume, of the aforementioned total pore volume is accounted for by the diameter ranges from 0 to <1.0 µm, from 1.0 to <10 µm and from 10 µm to 100 µm.

The inventive procedure is also advantageous when the pore diameter distributions according to EP-A 293 859 are present in the second-stage catalyst active compositions.

Every single statement made above on specific surface area, pore diameter, total pore volume and pore diameter distribution applies especially in relation to every single multimetal oxide composition mentioned as relevant in this document for catalysts of the first oxidation stage and of the second oxidation stage.

In principle, the volume-specific activity of the at least one first catalyst bed (especially fixed catalyst bed) within the first reaction stage in the process according to the invention may either be constant over the length of the flow path in flow direction of reaction gas mixture 1 or increase at least once (continuously or abruptly or in stages). At least one increase is preferred in accordance with the invention under the inventive criteria (minimum by-product formation). In all of the aforementioned cases, it is also advantageous when the active composition does not change over the length of the flow path within the first reaction stage.

The statements made above for the first reaction stage apply equally to the second reaction stage of the process according to the invention.

When the catalyst bed for the first reaction stage is a fixed catalyst bed, it is possible to prepare this fixed catalyst bed 1 in the process according to the invention by using only shaped catalyst bodies having multimetal oxide active composition or else substantially homogeneous mixtures of shaped catalyst bodies having multimetal oxide active composition and shaped bodies (shaped diluent bodies) which have no multimetal oxide active composition and behave substantially inertly with respect to the heterogeneously catalyzed partial gas phase oxidation. Useful materials for such inert shaped bodies are in principle all of those which are also suitable as support material for coated catalysts suitable in accordance with the invention. Useful such materials include, for example, porous or nonporous aluminum oxides, silicon dioxide, thorium dioxide, zirconium dioxide, silicon carbide, silicates such as magnesium silicate or aluminum silicate, or the steatite already mentioned.

The geometry of such inert shaped diluent bodies may in principle be as desired. In other words, they may be, for example, spheres, polygons, solid cylinders or else, like the shaped catalyst bodies having active composition, rings. Preferably in accordance with the invention, the inert shaped diluent bodies selected will be those whose geometry corresponds to that of the shaped catalyst bodies to be diluted with them (the above statements also apply to substantially homogeneous mixtures of shaped catalyst bodies having multimetal oxide active composition and shaped diluent bodies usable for the provision of a fixed bed catalyst charge 2 (fixed catalyst bed for the second reaction stage)).

It is advantageous when the chemical composition of the active composition used does not change over the fixed bed catalyst charge 1. In other words, the active composition used for an individual shaped catalyst body may be a mixture of different multimetal oxides, but the same mixture then has to be used for all shaped catalyst bodies of the fixed bed catalyst charge 1.

The volume-specific (i.e. normalized to the unit of volume) activity can be reduced in a simple manner by homogeneously diluting a basic amount of shaped catalyst bodies produced in a uniform manner with shaped diluent bodies. The higher the fraction of the shaped diluent bodies selected, the lower the amount of active composition, or catalyst activity, present in a certain volume of the bed.

A volume-specific activity increasing at least once in flow direction of the reaction gas mixture over fixed bed catalyst charge 1 can thus be attained for the process according to the invention in a simple manner, for example, by beginning the bed with a high fraction of inert shaped diluent bodies based on one type of shaped catalyst bodies, and then reducing this fraction of shaped diluent bodies in flow direction either continuously or, at least once or more than once, abruptly (for example in stages). When the content of shaped diluent bodies is left constant or no shaped diluent bodies at all are used additionally in fixed bed catalyst charge 1, the result is a constant volume-specific activity in flow direction of the reaction gas mixture over fixed bed catalyst charge 1. However, an increase in the volume-specific activity is also possible, for example, by, with constant geometry and active composition type of a shaped coated catalyst body, increasing the thickness of the active composition layer applied to the support, or, in a mixture of coated catalysts with the same geometry but with different proportion by weight of the active composition, increasing the proportion of shaped catalyst bodies with higher proportion by weight of active composition. A similar effect can also be achieved, for example, by, in mixtures of unsupported catalysts and of coated catalysts (with identical active composition) altering the mixing ratio in an appropriate manner. It will be appreciated that the variants described can also be employed in combination.

Normally, in the process according to the invention the volume-specific activity will decrease once neither within fixed bed catalyst charge 1 nor within fixed bed catalyst charge 2 in flow direction of the reaction gas mixture.

Upstream and/or downstream of fixed bed catalyst charge 1 may be disposed beds consisting exclusively of inert material (for example only shaped diluent bodies) (for terminology purposes, they are not included in the fixed bed catalyst charge 1 in this document, since they do not comprise any shaped bodies which have multimetal oxide active composition). The shaped diluent bodies used for the inert bed may have the same geometry as the shaped catalyst bodies used in fixed bed catalyst charge 1. However, the geometry of the shaped diluent bodies used for the inert bed may also be different from the aforementioned geometry of the shaped catalyst bodies (for example, spherical instead of annular).

Preferably in accordance with the invention, fixed bed catalyst charge 1 in the process according to the invention is structured in flow direction of the reaction gas mixture as follows.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst charge 1, either only shaped catalyst bodies or a homogeneous mixture of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, or from 10 to 40% by weight or from 20 to 40% by weight or from 25 to 35% by weight. Downstream of this first zone of fixed bed catalyst charge 1 is then disposed, advantageously in accordance with the invention, up to the end of the length of fixed bed catalyst charge 1 (i.e., for example, to a length of from 2.00 to 3.00 m, preferably from 2.50 to 3.00 m), either a bed of shaped catalyst bodies diluted only to a lesser extent (than in the first zone), or, most preferably, a sole (undiluted) bed of the same shaped catalyst bodies which have also been used in the first zone.

The aforementioned is especially true when the shaped catalyst bodies used in fixed bed catalyst charge 1 are unsupported catalyst rings or coated catalyst rings (especially those which are mentioned in this document as preferred). For the purposes of the aforementioned structuring, both the shaped catalyst bodies and the shaped diluent bodies in the process according to the invention advantageously have substantially the ring geometry 5 mm×3 mm×2 mm (external diameter× length×internal diameter).

In a manner corresponding to that in which the volume-specific activity of fixed bed catalyst charge 1 can be varied, the volume-specific activity of fixed bed catalyst charge 2 can also be varied. Upstream and/or downstream of the actual fixed bed catalyst charge 2 may again be disposed an appropriate inert bed.

Preferably in accordance with the invention, fixed bed catalyst charge 2 in the process according to the invention is structured as follows in flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst charge 2, either only shaped catalyst bodies or a homogeneous mixture of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone of fixed bed catalyst charge 2 is then disposed, advantageously in accordance with the invention, up to the end of the length of fixed bed catalyst charge 2 (i.e., for example, to a length of from 2.00 to 3.00 m, preferably from 2.50 to 3.00 m), either a bed of shaped catalyst bodies only to a lesser extent (than in the first zone), or, most preferably, a sole bed of the same shaped catalyst bodies which have also been used in the first zone.

The aforementioned is especially true when the shaped catalyst bodies used in fixed bed catalyst charge 2 are coated catalyst rings (especially those which are mentioned in this document as preferred). For the purposes of the aforementioned structuring, both the shaped catalyst bodies or their support rings and the shaped diluent bodies in the process according to the invention advantageously have substantially the ring geometry 7 mm×3 mm×4 mm (external diameter× length×internal diameter).

Appropriately in accordance with the invention, the first reaction stage of the process according to the invention can be carried out, for example, in a tube bundle reactor charged with fixed bed catalyst charge 1 (and, if appropriate, inert beds upstream and/or downstream of it), as described, for example, in EP-B 700714.

In other words, in the simplest manner, the aforementioned charge in each case is disposed in the individual metal tubes of a tube bundle reactor and a heating medium (one-section method), generally a salt melt, is conducted around the metal tubes. Salt melt and reaction gas mixture may be conducted in simple cocurrent or countercurrent. However, the salt melt (the heating medium) may also be conducted around the tube bundle in a meandering manner viewed over the reactor, so that only viewed over the entire reactor does a cocurrent or countercurrent to the flow direction of the reaction gas mixture exist. The flow rate of the heating medium (heat exchange medium) is typically such that the temperature rise (caused by the exothermicity of the reaction) of the heat exchange medium from the inlet point into the reactor to the outlet point from the reactor is from =0 to 10° C., frequently from =2 to 8° C., often from =3 to 6° C. The inlet temperature of the heat exchange medium into the tube bundle reactor is generally from 300 to 360° C., frequently from 300 to 340° C.

Suitable heat exchange media are especially fluid heating media. It is particularly favorable to use melts of salts such as potassium nitrate, potassium nitrite, sodium nitrite and/or sodium nitrate, or of low-melting metals such as sodium, mercury and alloys of different metals.

Typically, the catalyst tubes in the aforementioned tube bundle reactors are manufactured from ferritic steel and typically have a wall thickness of from 1 to 3 mm. Their internal diameter is (in particular in the case of use of the catalyst ring geometries specified in this document) generally from 20 to 30 mm, frequently from 21 to 26 mm. Their length is typically from 2 to 4 m, frequently from 2.5 to 3.5 m. According to the invention, normally at least 60%, frequently at least 75%, of these are occupied by fixed bed catalyst charge 1. Appropriately in a accordance with the invention, the number of catalyst tubes accommodated in the tube bundle vessel amounts to at least 5000, preferably to at least 10 000. Frequently, the number of catalyst tubes accommodated in the reaction vessel is from 15 000 to 30 000 or to 40 000. Tube bundle reactors having more than 50 000 catalyst tubes are usually the exception. Within the vessel, the catalyst tubes are normally arranged in homogeneous distribution, the distribution appropriately being selected such that the separation of the central internal axes of immediately adjacent catalyst tubes (known as the catalyst tube pitch) is from 35 to 45 mm (cf., for example, EP-B 468290). A tube bundle reactor suitable for the process according to the invention is also disclosed by DE-A 10131126, DE-A 10137768, DE-A 10135498 and DE-A 10232967.

Appropriately, starting reaction gas mixture 1 is fed to fixed bed catalyst charge 1 preheated to the reaction temperature. This purpose can be served, for example, by a bed of inert material preceding a fixed bed catalyst charge.

It will be appreciated that the first reaction stage of the process according to the invention may also be carried out in a two-section (or multisection) tube bundle reactor, as described, for example, in DE-A 19910508, 19948523, 19910506 and 19948241. A preferred variant of a two-section tube bundle reactor which can be used in accordance with the invention is disclosed by DE-C 2830765. However, the two-section tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed bed catalyst charge 1 to be used in accordance with the invention (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (reaction section A) in which the oxidative conversion of propene (in single pass) proceeds until a conversion in the range from 40 to 80 mol % is achieved, and a salt bath B flows around the section of the tubes (reaction section B) in which the subsequent oxidative conversion of propene (in single pass) proceeds until a conversion value of at least 90 mol % is achieved (if required, the reaction sections A, B to be used in accordance with the invention may be followed by further reaction sections which are maintained at individual temperatures).

It is appropriate from an application point of view for the first reaction stage of the process according to the invention not to comprise any further reaction sections. In other words, salt bath B appropriately flows around the section of the tubes in which the subsequent oxidative conversion of propene (in single pass) proceeds up to a conversion value of =90 mol %, or =92 mol %, or =94 mol %, or =96 mol % or more.

Typically, the beginning of reaction section B lies beyond the hotspot maximum of reaction section A. The hotspot maximum of reaction section B is normally below the hotspot maximum temperature of reaction section A.

According to the invention, both salt baths A, B can be conducted in cocurrent or in countercurrent through the space surrounding the reaction tubes relative to the flow direction of the reaction gas mixture flowing through the reaction tubes. It is of course also possible in accordance with the invention to employ cocurrent flow in reaction section A and countercurrent flow in reaction section B (or vice versa).

In all of the aforementioned cases, it is of course possible to superimpose a transverse flow on the parallel flow of the salt melt, relative to the reaction tubes, taking place within the particular reaction section, so that the individual reaction section corresponds to a tube bundle reactor as described in EP-A 700714 or in EP-A 700893, which results overall in a meandering flow profile of the heat exchange medium in a longitudinal section through the catalyst tube bundle.

In the two-section method too, starting reaction gas mixture 1 is appropriately fed preheated to the reaction temperature to fixed bed catalyst charge 1.

In the two-section tube bundle reactors too, the catalyst tubes are typically manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature section, the fixed bed catalyst charge 1 occupies at least 60%, or at least 75%, or at least 90%, of the length of the section. Any remaining length is, if appropriate, occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or to 40 000. Tube bundle reactors having a number of catalyst tubes above 50 000 are usually exceptional. Within the vessel, the catalyst tubes are normally arranged in homogeneous distribution, and the distribution is advantageously selected in such a way that the separation of the central internal axes of immediately adjacent catalyst tubes (known as the catalyst tube pitch) is from 35 to 45 mm (cf., for example, EP-B 468290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-section tube bundle reactors, the flow rate within the two heat exchange medium circuits required is selected in such a way that the temperature of the heat exchange medium rises from the inlet point into the reaction section to the outlet point from the reaction section (as a result of the exothermicity of the reaction) by from 0 to 15° C. In other words, the aforementioned ?T may, in accordance with the invention, be from 1 to 10° C., or from 2 to 8° C., or from 3 to 6° C.

According to the invention, the entrance temperature of the heat exchange medium into reaction section A is normally from 300 to 340° C. According to the invention, the entrance temperature of the heat exchange medium into reaction section B is normally firstly from 305 to 380° C., and is secondly simultaneously at least =0° C., or at least 5° C., above the entrance temperature of the heat exchange medium entering reaction section A. If appropriate, this temperature difference may also be =0° C.

At high propene loadings, the entrance temperature of the heat exchange medium into reaction section B is appropriately at least 10° C. above the entrance temperature of the heat exchange medium entering reaction section A. The difference between the entrance temperatures into reaction section A and B may, in accordance with the invention, thus be up to 20° C., up to 25° C., up to 30° C., up to 40° C., up to 45° C. or up to 50° C. Normally, the aforementioned temperature difference will, though, not be more than 50° C. The higher the propene loading on fixed bed catalyst charge 1 is selected in the process according to the invention, the greater should be the difference between the entrance temperature of the heat exchange medium into reaction section A and the entrance temperature of the heat exchange medium into reaction section B.

Advantageously, the entrance temperature of the heat exchange medium into reaction section B is, in accordance with the invention, from 330 to 370° C. and particularly advantageously from 340 to 370° C.

It will be appreciated that the two reaction sections A, B in the process according to the invention may also be realized in spatially separate tube bundle reactors. If required, a heat exchanger can also be mounted between the two reaction sections A, B.

It should also be pointed out once again here that, for an implementation of reaction stage 1 of the process according to the invention, it is possible in particular also to use the two-section tube bundle reactor type described in DE-B 2201528, which includes the possibility of removing a portion of the hotter heat exchange medium of reaction section B to reaction section A, in order if appropriate to heat a cold starting reaction gas mixture or a cold cycle gas. The tube bundle characteristics within an individual reaction section may also be configured as described in EP-A 382098.

According to the invention, it has been found to be appropriate to cool the product gas mixture leaving the first reaction stage before entry into the second reaction stage, in order thus to suppress subsequent complete combustion of parts of the acrolein formed in the first reaction stage. For this purpose, an after cooler is typically connected between the two reaction stages. In the simplest case, this may be an indirect tube bundle heat transferrer. In this case, the product gas mixture is generally conducted through the tubes and a heat exchange medium is conducted around the tubes, whose type may correspond to the heat exchange media recommended for the tube bundle reactors. Advantageously, the tube interior is filled with inert random packings (for example spirals of stainless steel, rings of steatite, spheres of steatite, etc). These improve the heat exchange and capture any molybdenum trioxide subliming out of the fixed bed catalyst charge of the first reaction stage before it enters the second reaction stage. It is advantageous for the after cooler to be manufactured from stainless steel coated with zinc silicate primer.

According to the invention, the resulting selectivity $S^{AA}$ of acrolein formation and of acrylic acid by-product formation (with increasing propylene conversion, $S^{AA}$ sometimes decreases slightly under otherwise identical conditions, since higher conversions normally require higher reaction temperatures) together in single pass in the first reaction stage will regularly be =85 mol % or =90 mol %, in many cases=92 mol % or =94 mol %, frequently=95 mol % or =96 mol % or = 97 mol %.

The process according to the invention is suitable for propene loadings of the fixed bed catalyst charge 1 of =80 l (STP)/l·h, or of =100 l (STP)/l·h, or of =120 l (STP)/l·h, or of = 140 l (STP)/l·h, or of =165 l (STP)/l·h, or of =170 l (STP)/l·h or =175 l (STP)/l·h or =180 l (STP)/l·h, but also for propene loadings of fixed bed catalyst charge 1 of =185 l (STP)/l·h, or = 190 l (STP)/l·h or =200 l (STP)/l·h or =210 l (STP)/l·h, and also for loading values of =220 l (STP)/l·h or = 230 l (STP)/l·h or =240 l (STP)/l·h or =250 l (STP)/l·h.

With increasing propane loading, the two-section method described is preferred over the one-section method described in the first reaction stage.

Normally, the propene loading of the first fixed bed catalyst charge in the process according to the invention will not exceed 600 l (STP)/l·h. Typically, the propene loadings of the fixed bed catalyst charge 1 in the process according to the invention are at values of =300 l (STP)/l·h, frequently at values of =250 l (STP)/l·h.

The working pressure in the process according to the invention in the first reaction stage may be either below standard pressure (for example up to 0.5 bar; the reaction mixture is sucked through) or above standard pressure. Typically, the working pressure in the first reaction stage is at values of from 1 to 5 bar, frequently from 1.5 to 3.5 bar. Normally, the reaction pressure in the first reaction stage will not exceed 100 bar.

Useful sources for the molecular oxygen required in the first reaction stage are both air and air depleted in molecular nitrogen.

It is appropriate from an application point of view to cool the product gas mixture of the first reaction stage to a temperature of from 210 to 290° C., frequently from 230 to 280° C. or from 250 to 270° C. in the after cooler already mentioned. The product gas mixture of the first reaction stage can quite possibly be cooled to temperatures which are below the temperature of the second reaction stage. However, the after cooling described is in no way obligatory and can generally be dispensed with especially when the path of the product gas mixture from the first reaction stage into the second reaction stage is kept short. Typically, the process according to the invention is also realized in such a way that the oxygen requirement in the second reaction stage is not already covered by an appropriately high oxygen content of starting reaction gas mixture 1, but rather that the oxygen required is added in the region between the first and second reaction stage. This can be done before, during, after and/or for after cooling. Useful sources for the molecular oxygen required in the second reaction stage are both pure oxygen and mixtures of oxygen and inert gas, for example air or air depleted in molecular nitrogen (for example=90% by volume of $O_2$, =10% by volume of $N_2$). The oxygen source is regularly added compressed to the reaction pressure. It will be appreciated that the oxygen requirement in the second reaction stage in the process according to the invention may already be covered by an appropriately high oxygen requirement in the first reaction stage.

The working pressure in the process according to the invention in the second reaction stage, as in reaction stage 1, may be either below standard pressure (for example up to 0.5 bar) or above standard pressure. According to the invention, the working pressure in the second reaction stage will typically be at values of from 1 to 5 bar, frequently from 1 to 3 bar. Normally, the reaction pressure in the second reaction stage will not exceed 100 bar.

Just like the first reaction stage, the second reaction stage of the process according to the invention can be carried out in a simple manner in a tube bundle reactor charged with fixed bed catalyst charge 2, as described, for example, in EP-A 700893. The inert beds preceding and/or following fixed bed catalyst charge 2 can complete the charge.

In other words, in the simplest manner, the fixed bed catalyst 2 to be used in accordance with the invention and any inert beds used additionally are disposed in the metal tubes of a tube bundle reactor and a heating medium (one-section mode), generally as salt melt, is conducted around the metal tubes. Salt melt and reaction gas mixture may be conducted in simple cocurrent or countercurrent. However, the heating medium may also be conducted around the tube bundle in a meandering manner viewed over the reactor, so that only viewed over the entire reactor does a cocurrent or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from =0 to 10° C., frequently from =2 to 8° C., often from =3 to 6° C. The entrance temperature of the heat exchange medium into the tube bundle reactor is generally from 230 to 300° C., frequently from 245 to 285° C., or from 255 to 275° C. Suitable heat exchange media are the same fluid heating media as have already been described for the first reaction stage.

Appropriately, starting reaction gas mixture 2 is fed to fixed bed catalyst charge 2 preheated to the reaction temperature. For the dimensioning of the catalyst tubes, the catalyst tube material, the catalyst tube number and its charge with fixed bed catalyst charge 2/inert bed, the same applies as was stated for the tube bundle reactor of the first reaction stage.

In general, a one-section method of the first reaction stage is combined with a one-section method of the second reaction stage, the relative flow of reaction gas mixture and heating medium in both stages being selected identically.

However, it will be appreciated that the second reaction stage of the process according to the invention may also, in a manner corresponding to the first reaction stage, be realized as two spatially successive reaction sections C, D, in which case the temperature of reaction section C (this always means the temperature of the entering salt bath or heat carrier in general) is appropriately from 230 to 270° C. and the temperature of reaction section D is from 250 to 300° C. and simultaneously at least =0° C., or at least =5° C., above the temperature of reaction zone C. If appropriate, this temperature difference may also be =0° C.

Reaction section C extends preferably up to an acrolein conversion of from 65 to 80 mol %. Moreover, the temperature of reaction section C is advantageously from 245 to 260° C. The temperature of reaction section D at high acrolein loadings is preferably from 5 to 10° C. above the temperature of reaction section C and is advantageously from 260 to 285° C. For the two-section method of the second reaction stage, with regard to the reactor, for the dimensioning of the catalyst tubes, the catalyst tube material, the catalyst tube number and their charge with fixed bed catalyst 2/inert bed, the statements made for the two-section tube bundle reactor of the first reaction stage also apply.

The higher the acrolein loading of fixed bed catalyst charge 2 is selected in the process according to the invention, the greater the preference for the two-section method over the one-section method and the greater the difference between the temperature of reaction section C and the temperature of reaction section D should be selected. Normally, the aforementioned temperature difference will, though, not be more than 40° C. In other words, the difference between the temperature of reaction section C and the temperature of reaction section D may, in accordance with the invention, be up to 15° C., up to 25° C., up to 30° C., up to 35° C. or up to 40° C.

In the process according to the invention, the selectivity of acrylic acid formation, based on the acrolein converted, will regularly be =90 mol %, or =92 mol %, or =94 mol %, frequently=95 mol % or =96 mol % or =97 mol %.

The process according to the invention is suitable for acrolein loadings of fixed bed catalyst charge 2 of =80 l (STP)/l·h, or of =100 l (STP)/l·h, or of =120 l (STP)/l·h, or of = 140 l (STP)/l·h or =150 l (STP)/l·h, or of =160 l (STP)/l·h or = 170 l (STP)/l·h, or =175 l (STP)/l·h or =180 l (STP)/l·h, but also at acrolein loadings of fixed bed catalyst charge 2 of= 185 l (STP)/l·h, or of =190 l (STP)/l·h or =200 l (STP)/l·h, or = 210 l (STP)/l·h, and also at loading values of =220 l (STP)/l·h, or = 230 l (STP)/l·h or 240 l (STP)/l·h, or =250 l (STP)/l·h.

Preferably in accordance with the invention, no secondary gas consisting only of inert gas is metered in between the first and second reaction stage.

Normally, the acrolein loading of the second fixed bed catalyst charge in the process according to the invention will not exceed the value of 600 l (STP)/l·h. Typically, the acrolein loadings of fixed bed catalyst charge 2 in the process according to the invention are, without significant loss of conversion and selectivity, at values of =300 l (STP)/l·h, frequently at values of =250 l (STP)/l·h.

In general, the acrolein loading of fixed bed catalyst charge 2 in the process according to the invention will be about 10 l (STP)/l·h, frequently about 20 or 25 l (STP)/l·h, below the propene loading of fixed bed catalyst charge 1. This is primarily attributable to the fact that both conversion and selectivity for acrolein in the first reaction stage generally do not attain 100%. Moreover, the oxygen demand of the second reaction stage is typically covered by air as a secondary gas. With increasing acrolein loading, the two-section method described is preferred over the one-section method performed in the second reaction stage.

Remarkably, the selectivity of acrylic acid formation assessed over both reaction stages in the process according to the invention, based on propene converted, even at the highest propene and acrolein loadings, may generally be at values of =83 mol %, frequently at =85 mol % or =88 mol %, often at =90 mol % or =93 mol % or more.

In an appropriate manner from an application point of view, the second reaction stage of the process according to the invention is carried out in a two-section tube bundle reactor. A preferred variant of a two-section tube bundle reactor usable in accordance with the invention for the second reaction stage is disclosed by DE-C 2830765. However, the two-section tube bundle reactors disclosed in DE-C 2513405, U.S. Pat. No. 3,147,084, DE-A 2201528, EP-A 383224 and DE-A 2903582 are also suitable for a performance of the second reaction stage of the process according to the invention.

In other words, in a simple manner, the fixed bed catalyst charge 2 (including any inert beds) to be used in accordance with the invention is disposed in the metal tubes of a tube bundle reactor and two substantially spatially separated heating media, generally salt melts, are conducted around the metal tubes. According to the invention, the tube section over which the respective salt bath extends represents a reaction section.

In other words, in a simple manner, for example, a salt bath C flows around those sections of the tubes (reaction section C) in which the oxidative conversion of acrolein (in single pass) proceeds until a conversion value in the range from 55 to 85 mol % is achieved, and a salt bath D flows around the section of the tubes (reaction section D) in which the subsequent oxidative conversion of acrolein (in single pass) proceeds until a conversion value of at least 90 mol % is achieved (if required, the reaction zones C, D to be used in accordance with the invention may be followed by further reaction zones which are maintained at individual temperatures).

It is appropriate from an application point of view for reaction stage 2 of the process according to the invention not to comprise any further reaction sections. In other words, salt bath D appropriately flows around the section of the tubes in which the subsequent oxidative conversion of acrolein (in single pass) proceeds up to a conversion value of =92 mol %, or =94 mol % or =96 mol % or =98 mol % and frequently even =99 mol % or more.

Typically, the beginning of reaction section D lies beyond the hotspot maximum of reaction section C. The temperature of the hotspot maximum of section D is normally below the hotspot maximum temperature of reaction section C.

According to the invention, both salt baths C, D can be conducted in cocurrent or in countercurrent through the space surrounding the reaction tubes relative to the flow direction of the reaction gas mixture flowing through the reaction tubes. It is of course also possible in accordance with the invention to employ cocurrent flow in reaction section C and countercurrent flow in reaction section D (or vice versa).

In all of the aforementioned cases, it is of course possible to superimpose a transverse flow on the parallel flow of the salt melt, relative to the reaction tubes, taking place within the particular reaction section, so that the individual reaction section corresponds to a tube bundle reactor as described in EP-A 700714 or in EP-A 700893, which results overall in a meandering flow profile of the heat exchange medium in a longitudinal section through the catalyst tube bundle.

Typically, the catalyst tubes in the aforementioned two-zone tube bundle reactors (Oust like in the tube bundle reactors of the one-zone method) are manufactured from ferritic steel and typically have a wall thickness of from 1 to 3 mm. Their internal diameter is generally from 20 to 30 mm, frequently from 22 to 26 mm. Their length is advantageously from 3 to 4 m, preferably 3.5 m. In each temperature zone, fixed bed catalyst charge 2 occupies at least 60%, or at least 75%, or at least 90%, of the length of the zone. Any remaining length is, if appropriate, occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or 40 000. Tube bundle reactors having a number of catalyst tubes above 50 000 are usually exceptional. Within the vessel, the catalyst tubes are normally arranged in homogeneous distribution, and the distribution is advantageously selected in such a way that the separation of the central internal axes of immediately adjacent catalyst tubes (known as the catalyst tube pitch) is from 35 to 45 mm (cf. EP-B 468290).

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-section tube bundle reactors, the flow rate within the two heat exchange medium circuits required is selected in such a way that the temperature of the heat exchange medium rises from the inlet point into the reaction zone to the outlet point from the reaction zone by from 0 to 15° C. In other words, the aforementioned ΔT may, in accordance with the invention, be from 1 to 10° C., or from 2 to 8° C., or from 3 to 6° C.

The entrance temperature of the heat exchange medium into reaction section C in an inventive two-section method in the second reaction stage is normally from 230 to 270° C. The entrance temperature of the heat exchange medium into reaction section D is, in accordance with the invention, normally firstly from 250 to 300° C. and is secondly simultaneously at least =0° C., or at least =5° C., above the entrance temperature of the heat exchange medium entering reaction section C.

At high acrolein loadings, the entrance temperature of the heat exchange medium into reaction section D is preferably from 5 to 10° C. above the entrance temperature of the heat exchange medium entering reaction section C. According to the invention, the difference between the entrance temperatures into reaction sections C and D may also be up to 15° C., up to 25° C., up to 30° C., up to 35° C. or up to 40° C. Normally, the aforementioned temperature will, though, not be more than 50° C. The higher the acrolein loading of catalyst bed 2 is selected in the process according to the invention, the greater should be the difference between the entrance temperature of the heat exchange medium into reaction section C and the entrance temperature of the heat exchange medium into reaction section D. The entrance temperature of the heat exchange medium into reaction section C is preferably from 245 to 260° C. and the entrance temperature into reaction section D from 260 to 285° C.

It will be appreciated that the two reaction sections C, D in the process according to the invention may also be realized in spatially separate tube bundle reactors. If required, a heat exchanger may also be mounted between the two reaction sections C, CD.

It should also be pointed out once again here that, for a performance of the second reaction stage of the process according to the invention, it is possible in particular also to use the two-section tube bundle reactor type which is described in DE-B 2201528 and includes the possibility of removing a portion of the hotter heat exchange medium of reaction section D to reaction section C, in order if appropriate to heat a starting reaction gas mixture 2 which is too cold or a cold cycle gas. The tube bundle characteristics within an individual reaction section may also be configured as described in EP-A 382 098.

It is of course also possible in the process according to the invention to combine two one-section tube bundle reactors for the two reaction stages to give a single two-section reactor to be operated in another manner, as described, for example, in DE-C 2830765, in EP-A 911313 and in EP-A 383 224. In this case, the first reaction stage is implemented in the first reaction section and the second reaction stage in the second reaction section of the two-zone tube bundle reactor.

In an entirely corresponding manner, it is also possible to combine one one-section tube bundle reactor and one two-section tube bundle reactor or two two-section tube bundle reactors to a single tube bundle reactor in each case which then has three or four temperature sections and is described, for example, in WO 01/36364.

In this case, for example, the first reaction stage can be carried out in the first reaction section and the second reaction stage in the two downstream reaction sections of the three-section tube bundle reactor. Alternatively, for example, the first reaction stage may be carried out in the first two reaction sections and the second reaction stage in the two downstream reaction sections of the four-section tube bundle reactor, and so forth. The salt bath temperature of the individual temperature sections may be configured as described in the case of the spatially separate tube bundle reactors. Normally, an inert bed is disposed in these cases between fixed bed catalyst charge 1 and fixed bed catalyst charge 2. However, it is also possible to dispense with such an intermediate inert bed. The length of the reaction tubes in the cases of combination in many cases corresponds to the sum of the lengths of the uncombined tube bundle reactors. The process according to the invention can of course also be performed analogously to the procedures described in the documents EP-A 990636 and EP-A 1 106 598.

In general, starting reaction gas mixture 1 in the process according to the invention comprises from 3 to 25% by volume, in many cases from 5 to 20% by volume and usually from 6 to 13% by volume of propylene.

According to the invention, the content of molecular oxygen in starting reaction gas mixture 1 should be such that the molar ratio $V_1$ of $O_2$ present in starting reaction gas mixture 1 to $C_3H_6$ present in the starting reaction gas mixture is $\geq 1$. Typically, $V_1$ in the process according to the invention is $\geq 1$ and $\leq 3$, usually $\geq 1.3$ and $\leq 2.5$, often from $\geq 1.5$ to $\leq 2.3$. The amount of molecular oxygen in starting reaction gas mixture 2 is normally such that the molar ratio of $O_2$ present in starting reaction gas mixture 2 to acrolein present in starting reaction gas mixture 2 is from $\geq 0.5$ to $\leq 2$, frequently from $\geq 0.75$ to $\leq 1.5$. It is favorable when product gas mixture 2 also comprises up to 5% by volume or up to 3% by volume of molecular oxygen.

Starting reaction gas mixture 1 may also comprise $\geq 0.01$, or $\geq 0.1$, or $\geq 0.5$, or $\geq 2\%$ by volume of $CO_2$. Usually, the aforementioned $CO_2$ content may be $\leq 25\%$ by volume.

Especially when the source used for the molecular oxygen in the process according to the invention is air, starting reaction gas mixture 1 will comprise molecular nitrogen as a further inert diluent gas. In principle, starting reaction gas mixture 1 in the process according to the invention may comprise $\geq 1\%$ by volume, or $\geq 5\%$ by volume, or $\geq 10\%$ by volume, or $\geq 20\%$ by volume, or $\geq 30\%$ by volume, or $\geq 40\%$ by volume of molecular nitrogen. In general, the content in starting reaction gas mixture 1 of molecular nitrogen will, however, be at values of $\leq 80$ mol %, or $\leq 70$ mol %, or $\leq 60$ mol %.

Essentially in accordance with the invention, starting reaction gas mixture 1 must comprise propane as an inert diluent gas. This propane content of starting reaction gas mixture 1 may be up to 70% by volume (for example, from 5 to 70% by volume), or up to 60% by volume, or to 50% by volume, or up to 40% by volume, or to 30% by volume, or to 20% by volume, or up to 10% by volume. Frequently, this propane content is $\geq 0.5$ or $\geq 1\%$ by volume. However, it may also be at values of $\geq 0.01\%$ by volume, or $\geq 0.02\%$ by volume, or $\geq 0.03\%$ by volume. In general, starting reaction gas mixture 1 comprises $\leq 10\%$ by volume, in many cases $\leq 5\%$ by volume of propane.

In the process according to the invention, this propane may, for example, be added deliberately as an inert diluent gas to be added separately to starting reaction gas mixture 1. Normally, this is done in the form of crude propane which, by its nature, may also comprise cyclopropane. As in the case of crude propylene, in order to achieve the target for starting reaction gas mixture 1 as per the claims, it is also possible here to remove cyclopropane present in the crude propane by rectification prior to use of the crude propane for the process according to the invention, or to convert it to propylene by passing the crude propane over suitable catalysts.

It will be appreciated that the propane may also become part of starting reaction gas mixture 1 by virtue of a partial dehydrogenation or oxydehydrogenation of propane (which are generally effected under heterogeneous catalysis) functioning as the propylene source for starting reaction gas mixture 1. In other words, the propylene present in starting reaction gas mixture 1 can be fed to starting reaction gas mixture 1 at least partly accompanied by unconverted propane from a partial dehydrogenation (for example homogeneously and/or heterogeneously catalyzed, in the presence and/or with exclusion of molecular oxygen). Appropriately in accordance with the invention, the crude propane to be used for such a partial dehydrogenation will likewise be subjected beforehand to a cyclopropane elimination.

In principle, the contents in starting reaction gas mixture 1 and of crude gases can be determined by gas chromatography without any problem. Analysis of condensed phase of starting reaction gas mixture 1 allows the detection limit for cyclopropane and other $C_3$ hydrocarbons to be extended.

The inventive procedure is particularly relevant when starting reaction gas mixture 1 comprises steam, since it promotes the conversion of cyclopropane.

The process according to the invention therefore comprises especially those embodiments in which starting reaction gas mixture 1 comprises from >0 to 35% by volume, frequently from 1 to 25% by volume, or from 5 to 15% by volume, or to 10% by volume of $H_2O$.

Typical starting reaction gas mixtures 1 are, for example, those which comprise:

| | |
|---|---|
| from 6 to 11% by volume of | propene, |
| from 6 to 12% by volume of | water, |
| from >0, frequently $\geq 0.5$ or $\geq 1$ to 10% by volume of | propane, |
| from $\geq 0$ to 5% by volume of | of constituents other than propene, propane, Water, oxygen, cyclopropane and nitrogen, |
| | sufficient molecular oxygen that $V_1$ is from 1 to 3, from $\geq 0$ up to $\geq 3$ mol %, based on propane present, of cyclopropane, and, |
| | as the remainder up to 100% by volume of the total amount of molecular nitrogen. |

In other words, inventive starting reaction gas mixtures 1 may also comprise:

| | |
|---|---|
| from 6 to 9% by volume of | propylene, |
| from 8 to 18% by volume of | molecular oxygen, |
| from 6 to 30% by volume of | propane and |
| from 32 to 72% by volume of | molecular nitrogen. |

Inventive starting reaction gas mixtures 2 may comprise:

| | |
|---|---|
| from 4.5 to 8% by volume of | acrolein, |
| from 2.25 to 9% by volume of | molecular oxygen, |
| from 6 to 30% by volume of | propane, |
| from 32 to 72% by volume of | molecular nitrogen, |
| from 5 to 30% by volume of | steam. |

However, inventive starting reaction gas mixtures 2 may also comprise up to 20% by volume of $H_2$.

In other words, reaction gas mixtures 1 of the process according to the invention may also comprise:

| | |
|---|---|
| from 4 to 25% by volume of | propylene, |
| from 6 to 70% by volume of | propane, |
| from 5 to 60% by volume of | $H_2O$, |
| from 8 to 65% by volume of | $O_2$ and |
| from 0.3 to 20% by volume of | $H_2$. |

The process according to the invention is also favorable when starting reaction gas mixture 1 comprises from 0.1 to 30% by volume of $CO_2$.

Starting reaction gas mixtures 2 possible in accordance with the invention may also comprise:

| | |
|---|---|
| from 3 to 25% by volume of | acrolein, |
| from 5 to 65% by volume of | molecular oxygen, |
| from 6 to 70% by volume of | propane, |
| from 0.3 to 20% by volume of | molecular hydrogen and |
| from 8 to 65% by volume of | steam. |

The acrylic acid can be removed from product gas mixture 2 as described in the prior art processes. To this end, the acrylic acid (normally accompanied by by-product propionic acid present in product gas mixture 2) is typically converted in a first separation zone from product gas mixture 2 into the condensed phase (in this document, the gas phase which generally remains is referred to as residual gas and may, if appropriate, comprise propylene unconverted in the partial oxidation). Useful processes for converting acrylic acid present in product gas mixture 2 to the condensed phase in separation zone 1 in the process according to the invention are in principle all processes known in this regard in the prior art. They essentially feature the conversion of the target product (the acrylic acid) by absorptive and/or condensative (cooling) measures from the gaseous to the condensed phase.

Useful absorbents are, for example, water, aqueous solution and/or organic (especially hydrophobic) solvents (cf. DE-A 103 36 386, DE-A 196 31 645, DE-A 195 01 325, EP-A 982 289, DE-A 198 38 845, WO 02/076917, EP-A 695 736, EP-A 778 225, EP-A 1 041 062, EP-A 982 287, EP-A 982 288, US 2004/0242826, EP-A 792 867, EP-A 784 046, EP-A 695 736 and the literature cited in this regard in these documents).

The acrylic acid present in product gas mixture 2 may also be converted to the condensed phase by full or else by fractional condensation (for example WO 04/035514, DE-A 199 24 532, DE-A 198 14 387, DE-A 197 40 253, DE-A 197 40 252, DE-A 196 27 847 and the literature cited in this regard in these documents).

Both the absorptive and the condensative conversion of acrylic acid to the liquid phase are typically undertaken in separation columns comprising separating internals (for enlarging the mass transfer surface area). Useful separating internals include all known internals. In other words, it is possible to use either trays such as bubble-cap trays, dual-flow trays or valve trays, random packings, for example Raschig rings, or structured packings, for example Sulzer packings, as separating internals. Product gas mixture 2 is generally conducted into the separation column ascending from the bottom upward. In the context of an absorptive condensation, the absorbent is normally moved (conducted) from the top downward in the separation column. The liquid absorbate running downward forms the condensed phase comprising the acrylic acid (and secondary components having a higher and similar boiling point, such as propionic acid). In the fractional condensation, the relatively high-boiling constituents of product gas mixture 2 are condensed ascending into it. The condensate comprising enriched acrylic acid is generally conducted out of the condensation column via side draw removal. It will be appreciated that absorption and condensation may also be employed superimposed on one another. This is, for example, always the case when heat is withdrawn additionally from the system in the absorption process by direct and/or indirect cooling.

Preference is given to conducting product gas mixture 2 into the separation column with a temperature reduced by indirect cooling, or by direct cooling or by direct and indirect cooling. The indirect cooling is undertaken in indirect heat exchangers in a manner known per se, while direct cooling is typically effected by spraying absorbent precooled in a quench apparatus or precooled bottoms liquid from the separation column into product gas mixture 2. A common feature of the above-described absorptive and/or condensative processes (separation processes) is that, at the top of the particular separation column comprising separating internals, into whose lower section product gas mixture 2, appropriately after preceding direct and/or indirect cooling thereof as described, is typically conducted, a residual gas stream normally remains which comprises mainly those constituents of product gas mixture 2 whose boiling point at standard pressure (1 bar) is $\leq -20°$ C. (i.e. the constituents which are difficult to condense or else volatile).

These include, for example, molecular nitrogen used additionally in the partial oxidation as an inert diluent gas, excess molecular oxygen remaining relative to the reaction stoichiometry in the partial oxidation, carbon oxides formed as a by-product or used additionally as inert diluent gases in starting reaction gas mixture 1, but also propylene unconverted in the partial oxidation and unconverted cyclopropane. In general, the remaining residual gas will, for example, also still comprise fractions of steam. Appropriately in accordance with the invention, at least a portion of such a residual gas will be recycled into the partial oxidation as a constituent of starting reaction gas mixture 1. Appropriately from an application point of view, such a cycle gas method can also be effected via a heterogeneously catalyzed partial dehydrogenation and/or oxydehydrogenation of propane upstream of the inventive partial oxidation as the propylene source. Frequently, in the process according to the invention, at least 10% by volume, or at least 20% by volume, or at least 30% by volume, but usually not more than 80% by volume, or not more than 60% by volume, or not more than 40% by volume of the residual gas will be recycled into the partial oxidation (but generally substantially fully, the total amount of unconverted propane and/or propene present therein and of unconverted cyclopropane with them). A portion of this recycling can also be effected into the second reaction stage, i.e. as a constituent of starting reaction gas mixture 2.

A cycle gas method carried out as described can firstly function as the inert gas source and generally increases the desired target product yield (based on amount of raw material used). It is also possible in principle to feed the entirety and/or a portion of the residual gas to incineration (for example for energy generation), as described, for example, in EP-A 925 272.

Absorptive and/or condensative removals of acrylic acid from product gas mixtures 2 are also described in the documents EP-A 1 388 533, EP-A 1 388 532, DE-A 102 35 847, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 195 01 325, DE-A 102 47 240, DE-A 197 40 253, EP-A 695 736, EP-A 1 041 062, EP-A 117 146, DE-A 43 08 087, DE-A 43 35 172, DE-A 44 36 243, DE-A 103 32 758 and DE-A 199 24 533.

An absorptive and/or condensative removal of acrylic acid from product gas mixture 2 can also be carried out as described in DE-A 103 36 386, DE-A 101 15 277, DE-A 196 06 877, EP-A 920 408, EP-A 1 068 174, EP-A 1 066 239, EP-A 1 066 240, WO 00/53560, WO 00/53561, DE-A 100 53 086, WO 01/96271, or as described in DE-A 10 2004 032 129 and its equivalent patents. Favorable removal methods are also the processes described in the documents WO 04/063138, WO 04/35514, DE-A 102 43 625 and DE-A 102 35 847. In principle, the acrylic acid can also be frozen out of product gas mixture 2 in the first separation zone.

The further removal of the acrylic acid from the condensed phase can thus be under-taken in a downstream separation zone 2 in the process according to the invention, depending on the procedure employed in separation zone 1 and depending on the specific process conditions which have been selected for the partial oxidation and thus determine the spectrum of other secondary components (reaction temperature, inert diluent gases selected, catalysts selected, content and molar ratio of the reactants in starting reaction gas mixture 1, etc.), up to the desired degree of purity of the acrylic acid by a wide variety of different combinations of a wide variety of different thermal separation processes. These may be, for example, combinations of extractive, desorptive, crystallizative, rectificative, azeotropically distillative, azeotropically rectificative, distillative and/or stripping processes.

It will be appreciated that all process steps performed in separation zones 1, 2 are carried out with inhibition of polymerization. The procedure may be as described in the prior art cited. An outstanding position among the entirety of the available acrylic acid process stabilizers is assumed by dibenzo-1,4-thiazine (PTZ), 4-hydroxy-2,2,6,6-tetramethylpiperidine-1-oxyl (4-OH-TEMPO) and p-methoxyphenol (MEHQ). They may, for example, each alone or in pairs or as a three-substance mixture, be part of the acrylic acid-containing liquid phase P to be treated crystallizatively in accordance with the invention. Typically, the total amount of polymerization inhibitors present in the liquor phase P, based on acrylic acid present therein, is from 0.001 to 2% by weight.

The reason for the advantage of the process according to the invention is that it permits, in a comparatively simple manner, the preparation of acrylic acid particularly low in or free of propionic acid, without necessarily requiring a crystallizative removal of acrylic acid in separation zone 2 for this purpose.

Finally, it should be emphasized once again that at least a portion of the residual gas remaining in the conversion (in separation zone 1) of the acrylic acid from product gas mixture 2 into the condensed phase can be recycled (as cycle gas) into the first reaction stage and/or into the second reaction stage.

This cycle gas may, if appropriate, comprise unconverted propylene. However, preferably in accordance with the invention, the propylene present in starting reaction gas mixture 1 will be added to the cycle gas to an extent of at least 25 mol %, better to an extent of at least 50 mol %, more preferably to an extent of at least 75 mol %, usually to an extent of at least 85 mol %, or to an extent of at least 90 or at least 95 mol % and in some cases even to an extent of 100 mol %, as crude propylene different from cycle gas.

When the propylene present in starting reaction gas mixture 1 is fed to starting reaction gas mixture 1 at least partly from a partial dehydrogenation (for example homogeneously and/or heterogeneously catalyzed, in the presence and/or with exclusion of molecular oxygen) (normally accompanied by propane unconverted in the partial dehydrogenation), at least a portion of the residual gas remaining in the conversion of the acrylic acid from product gas mixture 2 into the condensed phase may be recycled into the partial dehydrogenation of propane.

Moreover, it should be emphasized that the present invention comprises processes in which the process according to the invention for preparing acrylic acid is followed by a process for free-radical polymerization (especially for preparing water-superabsorbing polyacrylic acids and/or their partly or fully neutralized alkali metal (preferably Na) salts), in which acrylic acid prepared in accordance with the invention is free-radically polymerized to prepare polymers.

The present invention also comprises processes in which the process according to the invention for preparing acrylic acid is followed by a process for preparing acrylic esters, in which acrylic acid prepared in accordance with the invention is esterified with alcohols (preferably alkanols, more preferably $C_1$- to $C_{12}$-alkanols) (generally under acid catalysis).

The process for esterification can in turn be followed by a process for free-radical polymerization, in which acrylic esters prepared in this way are polymerized.

EXAMPLE AND COMPARATIVE EXAMPLE

I. Two-stage heterogeneously catalyzed partial oxidation of propylene to acrylic acid in the absence and in the presence of cyclopropane A) General experimental setup of the reaction apparatus Reactor for the First Oxidation Stage (1st Reaction Stage)

The reactor consisted of a jacketed cylinder of stainless steel (cylindrical guide tube surrounded by a cylindrical outer vessel). The wall thicknesses were always from 2 to 5 mm.

The internal diameter of the outer cylinder was 91 mm. The internal diameter of the guide tube was approx. 60 mm.

At the top and bottom, the jacketed cylinder was concluded by a lid and base respectively.

The catalyst tube (total length 400 cm, internal diameter 26 mm, external diameter 30 mm, wall thickness 2 mm, stainless steel) was accommodated in the guide tube of the cylindrical vessel such that it just protruded in each case through the lid and base at the upper and lower end thereof (in a sealed manner). The heat exchange medium (salt melt consisting of 53% by weight of potassium nitrate, 40% by weight of sodium nitrite and 7% by weight of sodium nitrate) was enclosed in the cylindrical vessel. In order to ensure very uniform thermal boundary conditions at the outer wall of the catalyst tube over the entire length of catalyst tube within the cylindrical vessel (400 cm) the heat exchange medium was pumped in circulation by means of a propeller pump.

An electrical heater attached to the outer jacket regulated the temperature of the heat exchange medium to the desired level. Otherwise, there was air cooling.

Reactor charge: Viewed over the first-stage reactor, the salt melt and the charge gas mixture of the first-stage reactor were conducted in cocurrent. The charge gas mixture entered the first-stage reactor at the bottom. It was conducted into the reaction tube with a temperature of 165° C. in each case.

The salt melt entered the cylindrical guide tube at the bottom with a temperature $T^{in}$ and left the cylindrical guide tube at the top with a temperature $T^{out}$ which was up to 2° C. above $T^{in}$.

$T^{in}$ was adjusted so as to always give rise to a propylene conversion of 97.8±0.1 mol % in single pass at the outlet of the first oxidation stage.

Catalyst Tube Charge:

(from the bottom upward) Section A: length 90 cm
Preliminary bed of steatite spheres of diameter 4-5 mm.
Section B: length 100 cm
Catalyst charge of a homogeneous mixture of 30% by weight of steatite rings of geometry 5 mm×3 mm×2 mm (external diameter×length×internal diameter) and 70% by weight of unsupported catalyst from section C.
Section C: length 200 cm
Catalyst charge of annular (5 mm×3 mm×2 mm=external diameter×length×internal diameter) unsupported catalyst according to example 1 of DE-A 100 46 957 (stoichiometry: $[Bi_2W_2O_9 \cdot 2WO_3]_{0.5}[Mo_{12}Co_{5.5}Fe_{2.94}Si_{1.59}K_{0.08}O_x]_1)$.
Section D: length 10 cm
Downstream bed of steatite rings of geometry 7 mm×3 mm×4 mm (external diameter×length×internal diameter)
Intermediate cooling and intermediate oxygen feeding (pure $O_2$ as secondary gas)

For the purpose of intermediate cooling (indirectly by means of air), the product gas mixture 1 leaving the first fixed bed reactor was conducted through a connecting tube (length 40 cm, internal diameter 26 mm, external diameter 30 mm, wall thickness 2 mm, stainless steel, wound around by 1 cm of insulating material) which was mounted centrally to a length of 20 cm, charged with an inert bed of steatite rings of geometry 7 mm×3 mm×4 mm (external diameter×length×internal diameter) and was flanged directly onto the first-stage catalyst tube.

The product gas mixture 1 always entered the connecting tube at a temperature of $>T^{in}$ (first stage) and left it with a temperature above 200° C. and below 270° C.

At the end of the connecting tube, molecular oxygen at the pressure level of product gas mixture 1 was metered into the cooled product gas mixture 1. The resulting gas mixture (charge gas mixture for the second oxidation stage) was conducted directly into the second-stage catalyst tube to which the abovementioned connecting tube was likewise flanged by its other end. The amount of molecular oxygen metered in was such that the molar ratio of $O_2$ present in the resulting gas mixture to acrolein present in the resulting gas mixture was 1.3.

Reactor for the Second Oxidation Stage (2nd Reaction Stage)

A catalyst tube fixed bed reactor was used which was of identical design to that for the first oxidation stage. Salt melt and charge gas mixture were conducted in cocurrent viewed over the reactor. The salt melt entered at the bottom, the charge gas mixture likewise. The inlet temperature $T^{in}$ of the salt melt was adjusted so as always to result in an acrolein conversion of 99.3±0.1 mol % in single pass at the outlet of the second oxidation stage. $T^{out}$ of the salt melt was always up to 2° C. above $T^{in}$.

The catalyst tube charge (from the bottom upward) was:

Section A: Length 70 cm
Upstream bed of steatite rings of geometry 7 mm×3 mm×4 mm (external diameter×length×internal diameter).
Section B: Length 100 cm
Catalyst charge of a homogeneous mixture of 30% by weight of steatite rings of geometry 7 mm×3 mm×4 mm (external diameter×length×internal diameter) and 70% by weight of coated catalyst from section C.
Section C: Length 200 cm
Catalyst charge of annular (7 mm×3 mm×4 mm=external diameter×length×internal diameter) coated catalyst according to preparation example 5 of DE-A 10046928 (stochiometry: $Mo_{12}V_3W_{1.2}Cu_{2.4}O_x$).
Section D: Length 30 cm
Downstream bed of steatite spheres of diameter 4-5 mm.
B) Results achieved as a function of the composition of starting reaction gas mixture 1 of the first oxidation stage (the propene loading was set to 150 l (STP)/l·h; the selectivity of acrylic acid formation (assessed over both reaction stages based on propylene converted) was always ≧94 mol %).

The composition of the gas mixture starting reaction for the first oxidation stage was substantially (based on the total volume of starting reaction gas mixture 1):

| | |
|---|---|
| 6.3% by vol. of | propylene, |
| 28% by vol. of | propane, |
| X % by vol. of | cyclopropane, |
| 10.8% by vol. of | $O_2$, |
| 5% by vol. of | $H_2O$ and, |
| | as the remainder, $N_2$. |

From product gas mixture 2, the acrylic acid formed was condensed out by direct cooling with condensate which had been formed beforehand, cooled to 4° C. and polymerization-inhibited with hydroquinone. The table below shows the proportion by weight Y of the amount of propionic acid present in the condensate, based on the amount of acrylic acid present therein as a function of the amount X* of cyclopropane present in starting reaction gas mixture 1, but reported here in mol % relative to the molar amount of propylene present in the starting reaction gas mixture.

TABLE

| X* (mol %) | Y (ppm by wt.) |
|---|---|
| 0.063 | 483 |
| 0.95 | 1114 |

Numerous modifications and variations on the present invention are obviously possible in light of the above disclosure and thus the present invention may be practiced otherwise than as specifically described herein without departing from spirit and scope of the present invention. Accordingly, it is therefore to be understood that the foregoing disclosure is merely illustrative of exemplary aspects of the present invention and that numerous modifications and variations can be readily made by skilled artisans that fall within the scope of the accompanying claims.

What is claimed is:

1. A process for heterogeneously catalyzed partial gas phase oxidation of propylene to acrylic acid, in which, in a first reaction zone, a starting reaction gas mixture 1 which comprises propylene and molecular oxygen as reactants and at least propane as an inert diluent gas and comprises the molecular oxygen and the propylene in a molar $O_2:C_3H_6$ ratio of ≧1 is first, in a first reaction stage at elevated temperature, conducted through at least one first catalyst bed whose catalysts have at least one multimetal oxide comprising Mo, Fe and Bi as the active composition in such a way that the propylene conversion in single pass through the catalyst bed is ≧90 mol % and the accompanying selectivity $S^{AC}$ of acrolein formation and of acrylic acid by-product formation together is ≧80 mol %, optionally the temperature of the product gas mixture 1 leaving the first reaction stage is reduced by direct cooling or by indirect cooling or by direct and indirect cooling, and, optionally secondary gas in the form of molecular oxygen or inert gas or molecular oxygen and inert gas is added to product gas mixture 1, and then product gas mixture 1, as a starting reaction gas mixture 2 which comprises acrolein and molecular oxygen as reactants and at least propane as an inert diluent gas and comprises the molecular oxygen and the acrolein in a molar $O_2:C_3H_4O$ ratio of ≧0.5, in a second reaction stage at elevated temperature and with formation of a product gas mixture 2, is conducted through at least one second catalyst bed whose catalysts have at least one multimetal oxide comprising Mo and V as the active composition in such a way that the acrolein conversion in single pass through the catalyst bed is ≧95 mol % and the selectivity $S^{AA}$ of acrylic acid formation assessed over both reaction stages, based on propylene converted, is ≧70 mol %, wherein starting reaction gas mixture 1, based on the molar amount of propane present therein, comprises ≦3 mol % of cyclopropane and has been obtained by adding the propylene required for the process as a constituent of crude propylene which consists of propylene to an extent of ≧90% by weight and of propane and propylene to an extent of ≧97% by weight.

2. The process according to claim 1, wherein the acrolein conversion in single pass through the catalyst bed is ≧96 mol %.

3. The process according to claim 1, wherein the acrolein conversion in single pass through the catalyst bed is ≧97 mol %.

4. The process according to claim 1, wherein the acrolein conversion in single pass through the catalyst bed is ≧98 mol %.

5. The process according to claim 1, wherein the acrolein conversion in single pass through the catalyst bed is ≧99 mol %.

6. The process according to claim 1, wherein starting reaction gas mixture 1, based on the amount of propane present therein, comprises ≦2 mol % of cyclopropane.

7. The process according to claim 1, wherein starting reaction gas mixture 1, based on the amount of propane present therein, comprises ≦1 mol % of cyclopropane.

8. The process according to claim 1, wherein starting reaction gas mixture 1, based on the amount of propane present therein, comprises ≦0.2 mol % of cyclopropane.

9. The process according to claim 1, wherein starting reaction gas mixture 1, based on the amount of propane present therein, comprises ≦0.15 mol % of cyclopropane.

10. The process according to claim 1, wherein the propylene conversion in single pass through the catalyst bed is ≧92 mol %.

11. The process according to claim 1, wherein the propylene conversion in single pass through the catalyst bed is ≧94 mol %.

12. The process according to claim 1, wherein starting reaction gas mixture 1, based on the amount of propane present therein, comprises ≧10 molppb of cyclopropane.

13. The process according to claim 1, wherein starting reaction gas mixture 1, based on the amount of propane present therein, comprises ≧50 molppb of cyclopropane.

14. The process according to claim 1, wherein starting reaction gas mixture 1, based on the amount of propane present therein, comprises ≧1 molppm of cyclopropane.

15. The process according to claim 1, wherein the at least one multimetal oxide comprising Mo, Fe and Bi is one of the formula IV:

$$Mo_{12}Bi_aFe_bX_c^1X_d^2X_e^3X_f^4O_n \qquad (IV)$$

where
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5,
c=from 0 to 10,
d=from 0 to 2,
e=from 0 to 8,
f=from 0 to 10, and
n=a number which is determined by the valency and frequency of the elements in IV other than oxygen.

16. The process according to claim 1, wherein the at least one multimetal oxide comprising Mo and V is one of the formula VII:

$$Mo_{12}V_aX_b^1X_c^2X_d^3X_e^4X_f^5X_g^6O_n \qquad (VII)$$

where
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40, and
n=a number which is determined by the valency and frequency of the elements in VII other than oxygen.

17. The process according to claim 1, wherein the volume-specific activity of the at least one first catalyst bed increases at least once over the length of the flow path in flow direction of starting reaction gas mixture 1.

18. The process according to claim 1, wherein the volume-specific activity of the at least one second catalyst bed increases at least once over the length of the flow path in flow direction of starting reaction gas mixture 2.

19. The process according to claim 1, wherein the at least one first catalyst bed is a fixed bed and its propene loading is ≧120 l (STP)/l·h and ≦250 l (STP)/l·h.

20. The process according to claim 1, wherein starting reaction gas mixture 1 comprises from 6 to 13% by volume of propylene.

21. The process according to claim 1, wherein starting reaction gas mixture 1 comprises from >0 to 35% by volume of $H_2O$.

22. The process according to claim 1, wherein starting reaction gas mixture 1 comprises from ≧0.01% by volume of propane.

23. The process according to claim 1, wherein starting reaction gas mixture 1 comprises from ≧1% by volume of propane.

24. The process according to claim 1, wherein starting reaction gas mixture 1 comprises from $\geq 5$ to $\leq 70\%$ by volume of propane.

25. The process according to claim 1, wherein starting reaction gas mixture 1 comprises from $\geq 0.01\%$ by volume of $CO_2$.

26. The process according to claim 1, wherein starting reaction gas mixture 1 comprises from $\geq 1\%$ by volume of $N_2$.

27. The process according to claim 1, wherein the acrylic acid is removed in a separation zone 1 from product gas mixture 2 by conversion to the condensed phase.

28. The process according to claim 27, wherein the acrylic acid is converted from product gas mixture 2 into the condensed phase by absorptive measures.

29. The process according to claim 27, wherein the acrylic acid is converted from product gas mixture 2 into the condensed phase by condensative measures.

30. The process according to claim 27, wherein the acrylic acid is converted from product gas mixture 2 into the condensed phase by absorptive and condensative measures.

31. The process according to claim 28, wherein the absorbent used is water or an aqueous solution.

32. The process according to claim 27, wherein the acrylic acid is removed in a separation zone 2 using at least one thermal separation process from the condensed phase obtained in separation zone 1.

33. The process according to claim 27, wherein at least a portion of the residual gas remaining in the conversion of the acrylic acid from product gas mixture 2 into the condensed phase is recycled into the first reaction stage and/or into the second reaction stage.

34. The process according to claim 1, wherein the propylene present in starting reaction gas mixture 1 is fed to starting reaction gas mixture 1 at least partly from a partial dehydrogenation of propane.

35. The process according to claim 34, wherein at least a portion of the residual gas remaining in the conversion of the acrylic acid from product gas mixture 2 into the condensed phase is recycled into the partial dehydrogenation of propane.

36. The process according to claim 1, which is followed by a process for preparing polymers in which acrylic acid prepared by the process according to claim 1 is polymerized.

37. The process according to claim 1, which is followed by a process for preparing acrylic esters in which acrylic acid prepared by the process according to claim 1 is esterified with an alcohol.

38. The process according to claim 37, which is followed by a process for preparing polymers in which acrylic ester prepared by the process according to claim 37 is polymerized.

* * * * *